United States Patent
Jehanli

(10) Patent No.: US 7,888,040 B2
(45) Date of Patent: Feb. 15, 2011

(54) DETECTION OF METHAMPHETAMINE GROUP DRUGS

(75) Inventor: Ahmed Mohammed Taki Jehanli, Abingdon (GB)

(73) Assignee: Concateno UK Limited, Abingdon, Oxfordshire (GB)

( * ) Notice: Subject to any disclaimer, the term of this patent is extended or adjusted under 35 U.S.C. 154(b) by 688 days.

(21) Appl. No.: 11/629,603

(22) PCT Filed: Jun. 10, 2005

(86) PCT No.: PCT/GB2005/050087
§ 371 (c)(1),
(2), (4) Date: Nov. 21, 2007

(87) PCT Pub. No.: WO2005/121793
PCT Pub. Date: Dec. 22, 2005

(65) Prior Publication Data
US 2008/0286816 A1    Nov. 20, 2008

(30) Foreign Application Priority Data
Jun. 14, 2004    (GB) ................................ 0413225.4

(51) Int. Cl.
*G01N 33/53* (2006.01)
(52) U.S. Cl. ...................... 435/7.1; 435/7.93; 435/7.95; 436/514; 436/518; 436/808; 436/810; 436/815; 436/816; 564/381
(58) Field of Classification Search ................ 436/514, 436/518, 808, 809, 810, 815, 816; 435/7.1, 435/7.93, 7.95
See application file for complete search history.

(56) References Cited

U.S. PATENT DOCUMENTS

| 3,996,344 A | 12/1976 | Gross |
| 4,016,146 A | 4/1977 | Soares |
| 4,041,076 A | 8/1977 | Avenia et al. |
| 4,067,774 A | 1/1978 | Rubenstein et al. |
| 4,329,281 A | 5/1982 | Christenson et al. |

(Continued)

FOREIGN PATENT DOCUMENTS

CN           1410770 A           4/2003

(Continued)

OTHER PUBLICATIONS

Braithwaite et al., Annals of Clinical Biochemistry (1995) 32:123-153.

(Continued)

*Primary Examiner*—Bao-Thuy L Nguyen
(74) *Attorney, Agent, or Firm*—Swanson & Bratschun, LLC

(57) ABSTRACT

The present invention provides immunoassays which are highly specific for detection in biological samples of methamphetamine and other drugs of abuse of the methamphetamine group such as ecstasy and other ecstasy class drugs. More particularly, competitive assays are provided comprising: (a) contacting said sample with (i) a pseudoephedrine/carrier conjugate in which pseudoephedrine is linked via its hydroxyl group to the carrier and (ii) an antibody which is capable of binding both one or more drugs of the methamphetamine group and said conjugate; and (b) determining whether the binding of said antibody to said conjugate is reduced by the presence of said sample, a reduction in binding being indicative that the sample contains a methamphetamine group drug.

30 Claims, 4 Drawing Sheets

U.S. PATENT DOCUMENTS

| | | | |
|---|---|---|---|
| 4,771,005 A | 9/1988 | Spiro | |
| 4,843,020 A | 6/1989 | Woodford | |
| 5,248,791 A | 9/1993 | Brynes et al. | |
| 5,279,955 A | 1/1994 | Pegg et al. | |
| 5,354,693 A * | 10/1994 | Brynes et al. | 436/537 |
| 5,677,132 A | 10/1997 | Strahilevitz | |
| 6,326,159 B1 | 12/2001 | Ullman et al. | |
| 6,991,911 B2 * | 1/2006 | Zheng et al. | 435/7.9 |
| 2003/0207469 A1 | 11/2003 | Rouhani et al. | |
| 2009/0017555 A1 | 1/2009 | Jehanli et al. | |

FOREIGN PATENT DOCUMENTS

| | | | |
|---|---|---|---|
| EP | 0279213 | 8/1988 | |
| EP | 0359063 | 3/1990 | |
| EP | 0371253 | 6/1990 | |
| EP | 0560411 | 9/1993 | |
| EP | 1167976 | 1/2002 | |
| EP | 1 178 316 | 2/2002 | |
| EP | 0560410 | 10/2002 | |
| EP | 0291194 | 7/2003 | |
| EP | 1340981 | 9/2003 | |
| EP | 1 825 262 | 8/2007 | |
| GB | 2339615 | 2/2000 | |
| GB | 2 404 023 | 1/2005 | |
| GB | 2404022 | 1/2005 | |
| WO | WO 88/08534 | * | 11/1988 |
| WO | WO-00/04381 | 1/2000 | |
| WO | WO-02/057739 | 7/2002 | |
| WO | WO-2005/090987 | 9/2005 | |
| WO | WO 2006/003472 | 1/2006 | |

OTHER PUBLICATIONS

International Search Report for PCT/GB2005/050087, mailed on Dec. 30, 2005, 2 pages.
Jehanli et al., J. of Forensic Sciences (2001) 46:1214-1220.
Pichini et al., Clinical Pharmacokinetics (1996) 30:211-228.
Rollins et al., Forensic Science Review (1997) 9:23-25.
Stout et al., J. of Analytical Toxicology (2003) 27:265-269.
Stout et al., J. of Forensic Sciences (2004) 49:160-164.

* cited by examiner (+)-Amphetamine (+)- Methamphetamine (+)- Ephedrine (-)- Ephedrine (+)- Pseudoephedrine (-)- Pseudoephedrine Tyramine Phenylpropanolamine

MDMA

MBDB

MDEA

MDA

Phentermine

Beta-phenylethylamine

DETECTION OF METHAMPHETAMINE GROUP DRUGS

CROSS-REFERENCE TO RELATED APPLICATIONS

This application is the national phase of PCT application PCT/GB2005/050087 having an international filing date of Jun. 10, 2005, which claims priority from British application number 0413225.4 filed Jun. 14, 2004. The contents of these documents are incorporated herein by reference.

The invention relates to the detection of methamphetamine and the designer ecstasy class of drugs in test samples, such as derived from biological matrices, environmental compositions and surfaces. In particular, the invention relates to procedures and reagents for use in the laboratory and for point-of-care and on-site testing for such drugs.

BACKGROUND OF THE INVENTION

Methamphetamine is an addictive and powerful stimulant of the central nervous system as well as the peripheral nervous system. It is similar in action to amphetamine, but is more potent. Both drugs are derivatives of phenylethylamine (see FIG. 1), as are the designer methamphetamine class of drugs including ecstasy (3,4-methylenedioxymethamphetamine, MDMA), (+/−)-N-methyl-1-(3,4-methylenedioxyphenyl)-2-butanamine (MBDB) and (+/−)-3,4-methylenedioxyethylamphetamine (MDEA) and others. Due to their powerful stimulant effect, these drugs are heavily abused.

Such drugs are normally detected in urine, blood, sweat, oral fluid and hair. Different types of immunoassays are available for this purpose. The assays generally utilise antibodies (polyclonal and monoclonal) raised to amphetamine and methamphetamine by immunising animals with drug derivatives attached to a carrier protein (e.g. bovine serum albumin) via a functional group attached to the phenyl group of the drug, in particular the para-position. The immunoassay will then utilise these antibodies and the same drug derivatives linked to a label, which may be, for example, a protein, an enzyme, a radioactive label or a fluorescein label. Prior art publications in this area covering both the production of antibodies and labelled drug derivatives are numerous and related commercial immunoassays are available like the Abbott and Roche systems (EP 0371253, EP 0279213, EP 1167976, U.S. Pat. No. 4,329,281, U.S. Pat. No. 4,041,076, U.S. Pat. No. 4,067,774, U.S. Pat. No. 3,996,344, U.S. Pat. No. 4,016,146 and WO 02057739). Other ways of making specific antibodies utilise drug derivatives attached to a carrier protein via the aliphatic alkyl-end (utilising 4-aminobutyl amphetamine and 4-aminobutyl methamphetamine) (EP 0359063 and Analytical Biochemistry, 1999, volume 274, pages 118-124). The immunoassay is set up using this antibody and the same derivative attached to a label. Assays specific for the ecstasy-class of drugs have also been reported. US Patent 2003207469 assigned to Microgenics Corporation describes the use of an ecstasy drug analogue, a derivative of 2-amino-methylenedioxyphenyl, for attachment to a carrier protein for immunisation and a for production of labelled analogue.

It is desirable that immunoassays for methamphetamine and the ecstasy class of drugs show specificity for the illicit drugs. This is important as many phenylethylamine analogues are used in over-the-counter medicines like decongestants (cough mix). The list is large and includes: ephedrines, pseudoephedrines, phenylpropanolamine and phenylepherine. Some of the popular medicines are Sudafed®, Contact®, Vicks® inhaler and Primatine® tablets. In addition, compounds like tyramine (4-hydroxy-phenethylamine) (see FIG. 1) can be present naturally in biological samples being tested for amphetamines/methamphetamines. Immunoassays should desirably have less than 0.4% cross-reactivity with tyramine to be useful (EP 0371253). Presently known immunoassays utilising derivatives of ecstasy have the limitation of not being able to detect methamphetamine, especially at the low levels that may exist in biological fluids other than urine (e.g. oral fluid). Immunoassays based on using antibodies to the drug derivatives attached to a carrier protein via the phenyl ring suffer from lack of specificity for methamphetamine and are subject to interference by many of the licit drugs mentioned above. The Abbott assay requires prior sample treatment to eliminate or reduce undesirable cross-reactivity. Samples are treated with sodium periodate to eliminate cross-reactivity with drugs like ephedrines, pseudoephedrine and phenylpropanolamine as well as tyramine (EP 0371253). Over 40 medicines are listed as causing false positive results in methamphetamine urine tests (www.erowid.org/).

The lack of specificity of amphetamine/methamphetamine immunoassays has become a matter of concern (Journal of Analytical Toxicology, 2003, volume 27, pages 265-269, and references within). A recent study (Journal of Forensic Science, 2004, volume 49, pages 160-164) evaluating commercially available test kits for interference by ephedrine, pseudoephedrine and phenylpropanolamine showed an un-acceptable level of interference and concluded that manufacturers underestimate the level of undesirable cross-reactivity shown by their kits.

SUMMARY OF THE INVENTION

The present invention now provides immunoassays which are highly specific for detection in biological samples of methamphetamine and other drugs of abuse of the methamphetamine group such as ecstasy without significant interference from other phenyethylamine derivatives, which rely on use of a pseudoephedrine derivative, more particularly pseudoephedrine linked via its hydroxyl group to a carrier. The inventor surprisingly found that such a conjugate in which pseudoephedrine is linked to a carrier protein such as bovine serum albumin (BSA) reacted strongly with monoclonal antibodies to methamphetamine. Furthermore, and completely unexpectedly, binding of such an antibody to immobilised BSA-pseudoephedrine was found to be competitively inhibited by methamphetamine and ecstasy in biological fluids, but not significantly by (+/−)-pseudoephedrines, (+/−)-ephedrines and a number of other phenylethylamine analogues commonly recognised as potential interferents in detection of methamphetamine, including tyramine, even at relatively very high concentrations. This observation provides the foundation for new highly specific competitive type immunoassays for detection of methamphetamine, ecstasy and other drugs of abuse belonging to the methamphetamine group Accordingly, the invention provides a method for detecting whether a liquid sample contains one or more drugs of the methamphetamine group, especially at least methamphetamine, ecstasy, MBDB and MDEA, and most desirably at least methamphetamine, ecstasy and MBDB at about ≧15 to 30 ng/ml, comprising:

(a) contacting said sample with (i) a pseudoephedrine/carrier conjugate in which pseudoephedrine is linked via its hydroxyl group to the carrier and (ii) an antibody which is capable of binding both one or more drugs of the methamphetamine group and said conjugate; and (b) determining whether the binding of said antibody to said conjugate is reduced by the presence of said sample, a reduction in binding being indicative that the sample contains a methamphetamine group drug.

Typically, the antibody employed will be an anti-methamphetamine antibody which also binds other drugs of the methamphetamine group which are recognised as drugs of abuse, including ecstasy and the designer ecstasy class drugs MBDB and MDEA. This may be, for example, a monoclonal anti-methamphetamine antibody obtained by immunising mice with methamphetamine-bovine IgG conjugate such as obtainable from East Coast Biological, USA (catalogue No. DU300) and employed in the examples. However, it will be readily apparent that other antibodies may be employed as discussed further below.

The term "drug of the methamphetamine group" will be understood to include methamphetamine itself and other drugs which are classified with methamphetamine as addictive phenylethylamine-derivative stimulants, including ecstasy and other designer drugs of the ecstasy class including MBDB and MDEA, which may be the subject of drug abuse. Further information on such drugs may be obtained for example from Annals of Clinical Biochemistry (1995) Volume 32, pages 123-153. Compared to amphetamine, methamphetamine has a primary amino group substituted by a secondary amino group and this is also a feature of the drugs of abuse of the methamphetamine group as listed above and shown in FIG. 1. The term "drug of the methamphetamine group" will thus be understood to exclude amphetamine, 3,4-methylenedioxyamphetamine (MDA) and beta-phenylethylamine. It will also be understood to exclude ephedrines, pseudoephedrines, phenylpropanolamine, phentermine and tyramine, the structures of which are also given in FIG. 1. This list is not exhaustive but merely illustrative of phenylethylamine analogues which can be distinguished by assay methods of the invention from methamphetamine and other related drugs of abuse which it is desired to detect and can be classified as a "drug of the methamphetamine group".

More particularly, such an assay is capable of detecting all of methamphetamine, ecstasy (DMA), MBDB and MDEA but exhibiting less than 0.4% cross-reactivity with any of (+)- or (−)-ephedrine, (+)- or (−)-pseudoephedrine, phenylpropanolamine, phentermine, tyramine, amphetamine, MDA and beta-phenylamine at a concentration as high as 10,000 ng/ml in the sample. Cross-reactivity with ephedrines, pseudoephedrines, phenylpropanolamine, phentermine and tyramine may be less than 0.1% at the same concentration. Hence, the risk of false positives arising from any ephedrine, pseudoephedrine, phenylpropanolamine, phentermine or tyramine in a biological sample such as a urine sample or oral fluid sample is very low.

An assay method of the invention may, for example, take the format of a conventional competitive ELISA in which the antibody or the pseudoephedrine/carrier conjugate is immobilised on a solid support. Such an assay may alternatively take the form of a lateral flow immunochromatography assay employing a porous test strip. In this case, again the immobilised reagent for analyte detection may be immobilised antibody or immobilised pseudoephedrine/carrier conjugate.

DETAILED DESCRIPTION OF THE INVENTION

Pseudoephedrine Conjugates

Figure 1:
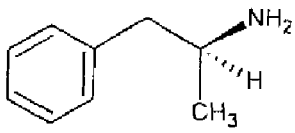
FIG. 1: Chemical structures of compounds illustrative of drugs of the methamphetamine group and of other compounds which are potential interferents in testing for such compounds by prior art methods.
Figure 1:
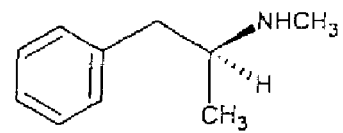
Figure 1:
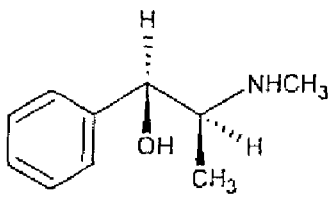
Figure 1:
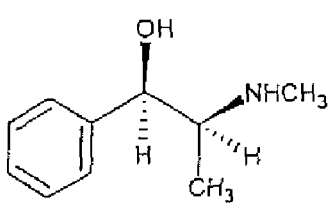
Figure 1:
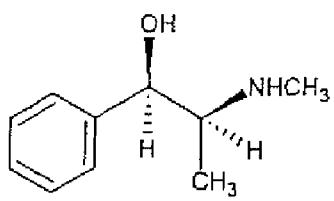
Figure 1:
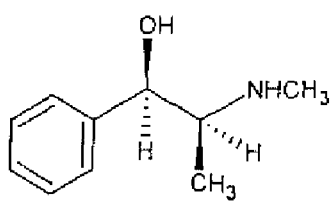
Figure 1:
Figure 1:
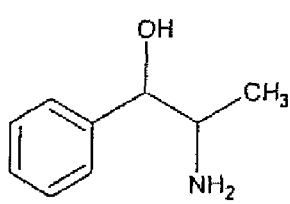
Figure 1:
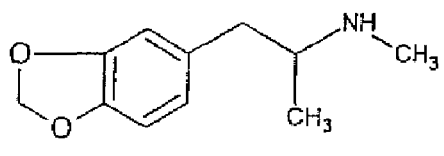
Figure 1:
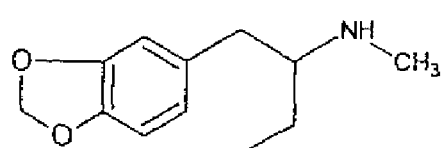
Figure 1:
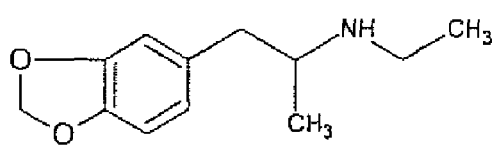
Figure 1:
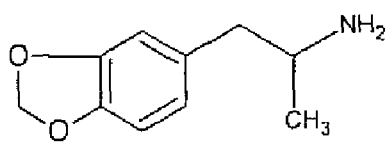
Figure 1:
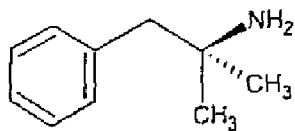
Figure 1:
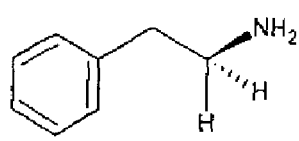

Suitable pseudoephedrine conjugates for use in carrying out assays according to the invention are any such conjugate wherein pseudoephedrine is linked via its hydroxyl group to a carrier such that is capable of binding antibodies to one or more drugs of the methamphetamine group. Desirably the pseudoephedrine conjugate will bind anti-methamphetamine antibody which is also capable of binding ecstasy and other ecstasy class drugs including MBDB and MDEA, e.g. monoclonal anti-methamphetamine antibody as supplied by East Coast Biological, USA. As already noted above, this antibody exemplifies suitable anti-methamphetamine antibodies obtainable by using as the immunogen a methamphetamine-protein conjugate. The pseudoephedrine may be (+)-pseudoephedrine or (−)-pseudoephedrine or a mixture of these.

In one embodiment, the carrier may be a protein. Any carrier protein may be used, including, for example, in addition to BSA, ovalbumin, gamma globulins (IgG) and thyroglobulin. A suitable carrier protein may be an enzyme, for example horseradish peroxidase. In this case, the carrier may also serve as a detectable label in an assay of the invention. In another embodiment, the carrier may be a homo- or heteropolymer containing amino acid side chains such as polylysine, polyornithine or poly-(glutamine, lysine).

The pseudoephedrine conjugate may also be labelled directly or indirectly with a detectable label which is not the carrier. In this case, the label may be joined to any portion of the conjugate whereby the ability to bind suitable antibodies is retained, e.g. a carrier protein. Suitable labels include, for example, radioisotopes such as $^{125}$I, $^{32}$P or $^{35}$S, particulate labels such as gold, fluorescent labels such as fluorescein, and biotin.

The carrier may be linked to the pseudoephedrine directly using a cross-linking reagent or via a spacer. Many cross-linking reagents are known for attaching hydroxyl groups to amino groups (for a review see "Bioconjugate Techniques" by G. T. Hermanson, 1996, Academic Press). Three such approaches for cross-linking pseudoephedrine to a carrier protein are given in the examples employing dimethyl aminopyridine/disuccinimidyl carbonate, formaldehyde and vinyl sulfone. However. other methods are equally suitable. Suitable spacers include aminocaproic acid spacers, aminohexane spacers and ethylamine spacers. The spacer may be attached to the carrier by any suitable mean. For example, where the carrier is a protein, the spacer may be attached to an amino side chain or carbohydrate moiety of the carrier protein.

Antibodies

As indicated above, a suitable antibody for use in a method of the invention will be capable of specifically binding to a pseudoephedrine conjugate as described above in which the pseudoephedrine is covalently conjugated to a carrier via its hydroxyl group and will also be capable of specifically binding to one or more methamphetamine group drugs. Preferably, the antibody employed will be capable of specifically binding all of methamphetamine, ecstasy (DMA), MBDB and MDEA. Most desirably, such binding will be such that at least all of methamphetamine, MDMA and MBDB are capable of detection at about ≧15 to 30 ng/ml, e.g. about ≧15 to 25 ng/ml in a competitive ELISA assay.

By "specifically binding" is meant that the antibody binds more strongly or preferentially to one or more drugs of the methamphetamine group in a competitive assay of the invention but shows little or no cross-reactivity, e.g. less than 0.4% cross-reactivity, with any of (+)-ephedrine, (−)-ephedrine, (+)-pseudoephedrine, (−)-pseudoephedrine, phenylpropanolamine, phentermine, tyramine, amphetamine, MDA and beta-phenylethylamine, for example at a concentration as high as 10,000 ng/ml. Desirably, the antibody will exhibit less than 0.1% cross-reactivity with ephedrines, pseudoephedrines, phenylpropanolamine, phentermine and tyramine at the same concentration, e.g. as determined by competitive ELISA assay as illustrated in the examples.

As also already indicated above, a suitable antibody may be, for example, a known commercially available anti-methamphetamine antibody, e.g. the monoclonal anti-methamphetamine antibody referred to above and in the examples. However, it will be appreciated that suitable antibodies, either polyclonal or monoclonal, may be produced by known techniques, e.g. using methamphetamine-protein conjugates.

It is envisaged that suitable antibodies may be generated by using as the immunogen a pseudoephedrine conjugate as described above in which the pseudoephedrine is linked to a carrier via its hydroxyl group. It is postulated that such linkage of pseudoephedrine to, for example, BSA causes change in configuration of the compound in such a way that antibodies can recognise this structure at a much higher affinity than free pseudoephedrine.

An antibody for use in a method of the invention may be labelled directly or indirectly, e.g. by means of secondary labelled antibodies. Suitable labels for this purpose are any label conventionally employed in immunoassays including radioactive labels, fluoresecent labels, enzyme labels such as horseradish peroxidase and biotin.

The term "antibody" as used herein will be understood to extend to antibody fragments, e.g. Fab, Fab' and Fv fragments, which retain antibody binding capability and might be utilised in a method of the invention Competitive Assays The present invention utilises pseudoephedrine conjugates and antibodies as described above in competitive immunoassays for the detection of one or more drugs of the methamphetamine group. It will be appreciated that the drugs detected will be determined by the specificity of the antibody employed, but as indicated above will desirably include methamphetamine, ecstasy, MBDB and MDEA. Especially preferred is an assay which detects methamphetamine and provides high cross-reactivity for ecstasy and MBDB, e.g. higher than 50% cross-reactivity at 15 to 25 ng/ml as determinable in a competitive ELISA assay.

A method of the invention may adopt any format for performing a competitive immunoassay. Drug-antibody binding may occur in solution followed by separation of bound complexed label. One of antibody capable of binding drug to be detected and pseudoephedrine conjugate may be bound to a solid support, e.g. a solid support comprising nitrocellulose or plastic, e.g. a plastic well surface, or solid beads, e.g. plastic or glass beads. A method of the invention may thus, for example, conform with a conventional competitive ELISA format. A suitable solid support for this purpose may be wells of a microtitre plate or solid beads. Alternatively, one of the antibody for drug binding or pseudoephedrine conjugate may be immobilised on a porous test strip or sheet suitable for lateral flow immunochromatography, e.g. a test strip or sheet comprising nitrocelluose. Such a test strip or sheet may be, for example, in the form of nitrocellulose bound to a backing support, e.g. plastic sheet. Such a test strip or sheet may be nitrocelluose card.

Suitable test samples will be in a liquid form to allow interaction with the antibody. A sample may be a fluid sample derived from a test subject, for example a sample consisting of, or derived from, urine, blood, sweat, oral fluid (saliva) or hair. The sample may be a diluted biological sample. Particularly preferred, for example, is use of buffer-diluted oral fluid e.g. oral fluid diluted in Cozart Oral Fluid Dilution Buffer (Cozart Bioscience product CR-BUFF). A suitable sample may be derived from an environmental source or swab, e.g. a swab contacted with oral fluid in the mouth or a surface suspected of drug contamination. The sample may be obtained by dissolving a powder to be tested for the presence of a drug of the methamphetamine group in buffer solution. References which may be referred to for sample preparation include "Drug Monitoring in Nonconventional Biological Fluids and Matrices" in Clinical Pharmacokinetics 1996, volume 30, pages 211-228 and "Testing for Drugs of Abuse in Hair" in Forensic Science Review 1997, volume 9, pages 23-25.

Competitive ELISA and lateral low immunochromatography tests according to the invention are now discussed below more fully.

Competitive ELISA

In one embodiment, such a method may be carried out by coating a suitable surface, for example microtitre wells, with a suitable pseudoephedrine conjugate as described herein, e.g. a BSA-pseudoephedrine conjugate in which pseudoephedrine is linked to BSA via its hydroxyl group. In this case, appropriate labelled antibody, typically an anti-methamphetamine antibody, will be contacted with the conjugate together with test sample. The antibody may be labelled directly, e.g. horseradish-peroxidase-labelled anti-methamphetamine antibody may be employed, or indirectly, e.g. by binding of secondary labelled antibodies. Alternatively, the surface will be coated with suitable antibody and detectable conjugate contacted with the surface along with the test sample. In this case, the carrier of the conjugate may also be, or comprise, a detectable label, e.g. the carrier may be a detectable enzyme such as horseradish peroxidase.

Lateral Flow Methods

Lateral flow immunochromatography tests according to the invention can be carried out using any known form of lateral flow device and relying on competitive antibody binding for analyte detection. Such tests may be carried out using the methodology as described in GB Patent 2339615 of Cozart Bioscience Limited, corresponding published International Application WO 00/04831 and Journal of Forensic Science 2001, volume 46, pages 1214-1220.

A common feature of lateral flow devices for analyte detection is provision of a test strip or sheet comprising a dry porous material such as nitrocellulose through which a liquid sample can be drawn to reach one or more spatially distinct analyte detection zones. Each such zone presents an immobilised specific binding reagent. For the purpose of a lateral flow immunochromatography test according to the invention, at least one such analyte detection zone will be provided which presents either a suitable pseudoephedrine conjugate or an antibody capable of binding such conjugate and one or more drugs of the methamphetamine group as discussed above Such a test strip or sheet will also have joined thereto, or integral thereto, a label release zone which is capable of releasing into liquid drawn into that zone either labelled antibody if said at least one analyte detection zone presents immobilised conjugate or detectable conjugate if said at least one analyte detection zone presents immobilised antibody. Such test strips suitable for carrying out lateral flow drug detection methods of the invention constitute a further aspect of the invention.

Thus, there is also provided by the invention a test strip or sheet for carrying out a lateral flow immunochromatography test having the following features:

(i) a strip or sheet comprising a dry porous material, preferably nitrocelluose, having immobilised thereon in an analyte detection zone a suitable pseudoephedrine conjugate as described above or a suitable antibody as described above; and (ii) joined to, or integral to, said strip or sheet providing said analyte detection zone a separate label release zone which is capable of releasing into liquid drawn into that zone either said antibody in labelled form, if said analyte detection zone presents immobilised pseudoephedrine conjugate, or, if said analyte detection zone presents immobilised antibody, detectable pseudoephedrine conjugate. Such detectable pseudoephedrine conjugate may be, for example, pseudoephedrine-protein conjugate labelled with gold or coloured latex particles The examples detail lateral flow immunochromatography tests according to the invention employing immobilised pseudoephedrine/carrier conjugate. It is also envisaged however, that a number of different immobilised antibodies having different specificities for different methamphetamine group drugs may be employed in separate analyte detection zones. In addition to at least one analyte detection zone for detection of one or more drugs of the methamphetamine group, a test strip or sheet for lateral flow tests according to the invention may also have one or more further analyte detection zones for detection of one or more further drugs or drug classes or groups.

It will be appreciated that in a lateral flow device, the label release zone will be proximal to the analyte detection zone(s) having regard to the direction of liquid flow. It may be in the form of a pad joined to a strip or sheet providing the analyte detection zone(s). Methods for providing in such a strip or sheet an integral label release zone are also well known. For example, a region of a nitrocelluose strip may be glazed, e.g. by depositing an aqueous sugar or cellulose solution and the thus glazed region contacted with the labelled reagent (see, for example, European Patent No. 0291194 and related European Patents 0560410 and 0560411).

A test strip or sheet for use in a lateral flow method of the invention may also further comprise a sample receiving member or pad proximal to the label release zone. Such a sample receiving member or pad may be made from any bilbous material capable of absorbing liquid rapidly.

Typically such a test strip or sheet will have, beyond the analyte detection zone(s) in the direction of intended liquid flow along the strip, i.e. distal to the analyte detection zone(s), a further detection zone presenting an immobilised specific binding reagent so as to provide a control zone. The control zone functions to indicate that the liquid of the sample has traversed the preceding analyte detection zone(s) under conditions suitable for analyte detection. For example, where labelled antibody is provided by the label release zone, the control zone may present an immobilised antibody that is capable of binding the labelled antibody.

Distal to the detection zones in the direction of intended liquid flow, a test strip or sheet of the invention may further comprise an absorbent waste pad (end or wicking pad).

The invention also extends to lateral flow devices incorporating a test strip or sheet for carrying out a method of the invention, e.g a portable screening device as described in WO 00/04381 of Cozart Bioscience Limited.

Kits

In a further aspect, the invention also provides kits for carrying out a competitive method of the invention comprising a suitable pseudoephedrine conjugate as described herein and an antibody capable of binding both said conjugate and one or more methamphetamine group drugs, e.g. an anti-methamphetamine antibody which also binds ecstasy class drugs including ecstasy, MBDB and MDEA. Either the pseudoephedrine conjugate or antibody may be directly labelled with a detectable label. In the case of the pseudoephedrine conjugate, as already indicated above, it may be possible for the carrier part of the conjugate to serve as a detectable label. Alternatively, means for indirectly labelling either the conjugate or drug-binding antibody may be provided, e.g. secondary labelled antibody. Either the conjugate or the antibody may be immobilised on a solid support. For example the kit may comprise either the conjugate or the antibody immobilised on a test strip as described above for carrying out lateral flow immunochromatography. Such a test strip may be inserted into a housing providing a window or windows over the analyte detections zone(s) or together with such a housing.

A kit of the invention may comprise other components. For example, where the test sample is to be collected from a test subject, the kit may further comprise a fluid collection means, e.g. an oral fluid collection device or swab, a vessel such as a vessel suitable for collection of blood or urine, and/or a pipette. A kit for use in an ELISA-based method may further comprise components selected from a washing solution and an enzyme substrate, e.g. tetramethylbenzidine (TMB) if a horseradish peroxidase label is employed. A kit for use in a lateral flow method may include a portable screening device into which a housing as described above may be fitted for detection of bound label in the detection zone(s) and digital display of the results. The following examples illustrate the invention.

EXAMPLES

Example 1a

Preparation of BSA-pseudoephedrine Using dimethyl aminopyridine/disuccinimidyl carbonate 10 mg of (+)-pseudo-ephedrine ((+)-(ψ)-ephedrine-HCl, product number E-2750, Sigma Co., Poole, England) or 8.0 mg of (−)-pseudoephedrine (Sigma-Aldrich product No. 287644) were dissolved in 0.4 ml of dimethylformamide (DMF). 88 mg of disuccinimidyl carbonate in 0.4 ml DMF were added dropwise to the ephedrine solution. Dimethyl aminopyridine (42 mg) in 0.4 ml acetone were added very slowly and dropwise to the above mixture. The solution was stirred overnight at room temperature in the dark. BSA (60 mg) was dissolved in 6 ml of 0.1 M sodium bicarbonate. The activated drug was added slowly to the BSA solution. The solution was kept stirring at room temperature overnight. The drug protein conjugate was then dialysed against phosphate buffered saline, pH 7.3 containing 0.05% sodium azide for 3 days with several changes of the buffer. Finally, the protein concentration was determined by Lowry protein assay and the conjugate stored at −20° C.

Example 1b

Preparation of BSA-aminocaproic acid-pseudoephedrine

In many cases of immunoassays for haptens, better antibody binding can be achieved by extending the distance between the hapten molecule and the carrier molecule to which it is attached. BSA with an attached spacer was prepared as follows: Dissolve BSA (200 mg) in 4 ml of 0.05 M MES/NaOH buffer, pH 5.0. Add aminocaproic acid (ACA) (200 mg). After the ACA is completely dissolved, add 100 mg of N-hydroxysuccinimide in dimethyl formamide (0.3 ml). Conjugation of the ACA to BSA was then initiated by the addition of 120 mg of the water-soluble carbodiimide cross-linker EDAC in 0.2 ml water. The mixture was stirred for 4 hours at room temperature then a further 40 mg of EDAC in 0.1 ml water were added and stirring continued overnight at room temperature. The BSA-ACA conjugate was separated from free ACA by gel filtration on a Sephadex® G-50 medium column using phosphate buffered saline, pH 7.3 for elution. The protein peak was pooled and dialysed against 0.15 M NaCl for 5 days changing the buffer every day. Finally, the concentration of the conjugate was determined by Lowry protein assay and the protein diluted to 10 mg/ml in 0.15 M NaCl and stored at −20° C.

BSA-ACA-pseudoephedrine was then prepared using the identical procedure to that described above for preparation of BSA-pseudoephedrine but using BSA-ACA in place of BSA.

Example 2

Preparation of BSA-pseudoephedrine Using formaldehyde

Bovine serum albumin (25 mg) was dissolved in 2.5 ml of 0.1 M MES/NaOH buffer, pH 5.0. 4.0 mg of (+)-pseudoephedrine-HCl or 3.2 mg of (−)-pseudoephedrine in 0.2 ml water were added. While stirring, 0.5 ml of 37% formaldehyde was added slowly. The solution was stirred overnight at room temperature. The drug-BSA conjugate was purified by gel filtration on a Sephadex® G50M column using phosphate buffered saline, pH 7.3 as the eluting buffer. The protein peak was pooled and protein concentration determined using Lowry protein assay.

Example 3

Preparation of BSA-pseudoephedrine Using vinyl sulfone Method (+) or (−)-pseudoephedrine was conjugated to bovine serum albumin using vinyl sulfone as described in Journal of Immunological Methods, 1995, 181:187-200.

Example 4

Preparation of Horseradish Peroxidase-Labelled Pseudoephedrine

Horseradish peroxidase (HRP, 22 mg) was dissolved in 1 ml of phosphate buffered saline, pH 7.3. 0.1 ml of 0.088 M sodium periodate were added slowly. The solution was stirred for 20 minutes. Oxidation was terminated by the addition of 0.1 ml of 1 M ethylene glycol. The oxidised enzyme was purified by gel filtration using Sephadex G-50M column and 2 mM citric acid/disodium phosphate buffer, pH 5.0 as the eluting buffer. The oxidised enzyme peak was pooled. 1M Sodium carbonate/bicarbonate buffer, pH 10.0 was then added to the enzyme solution to a final concentration of 0.1 M. Then 2 mg of ethylene diamine-HCl (ED) in 0.1 ml water were added and the coupling allowed to proceed for 4 hours at room temperature. 0.5 ml of sodium borohydride (5 mg/ml) were added to stabilise the bond between ethylene diamine and the enzyme. HRP-ED was then purified by gel filtration on a Sephadex G-50M column using 0.15 M NaCl as the eluting buffer.

HRP-ED was activated by vinyl sulfone and coupled to pseudoephedrine as described for BSA-vinyl sulfone-pseudoephedrine above.

Example 5

Enzyme-Linked Immunosorbent Assay (ELISA) for Methamphetamine

Figure 2:
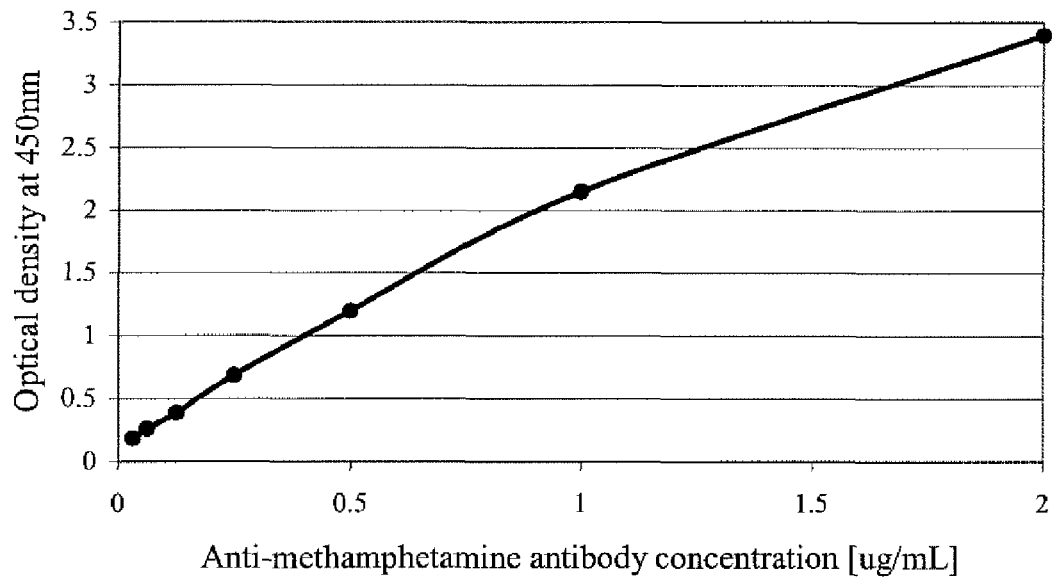
FIG. 2: Titration profile of anti-methamphetamine monoclonal antibody versus immobilised BSA-pseudoephedrine

Evaluation of BSA-Pseudoephedrine Conjugate:

The conjugate was evaluated using ELISA. 96-well microtitre plates (Costar) were coated with BSA-pseudoephedrine (5 :g/ml in 0.05 M sodium carbonate/bicarbonate buffer, pH 9.6, 100 :l/well) overnight at room temperature. The wells were then washed 3 times with phosphate buffered saline, pH 7.3, containing 0.05% Tween®-20 (wash buffer) and blocked in the same buffer for 30 minutes at room temperature. Two fold dilutions of monoclonal anti-methamphetamine antibody (East coast Biological, USA) in wash buffer containing 10 mg/ml BSA (assay buffer) were added to the wells (100 :l/well) and the plate incubated at room temperature for 30 minutes. The wells were washed 3 times with wash buffer and horseradish peroxidase-labelled goat anti-mouse IgG antibody (product number A-4416, Sigma Co., Poole, England) was added to the wells (1/2000 dilution in assay buffer, 100 :l/well) and incubation continued for a further 30 minutes. The wells were washed as before and the binding revealed by adding the enzyme substrate tetramethylbenzidine (TMB) to the wells (100 :l/well). After 30 minutes incubation, colour development was stopped by the addition of 1 M sulphuric acid (100 :l/well). Colour intensity was measured at 450 nm. FIG. 2 shows the titration profile of the monoclonal anti-methamphetamine antibody versus BSA-pseudoephedrine coated plate.

Competitive Inhibition ELISA (CELIA)

Figure 3:
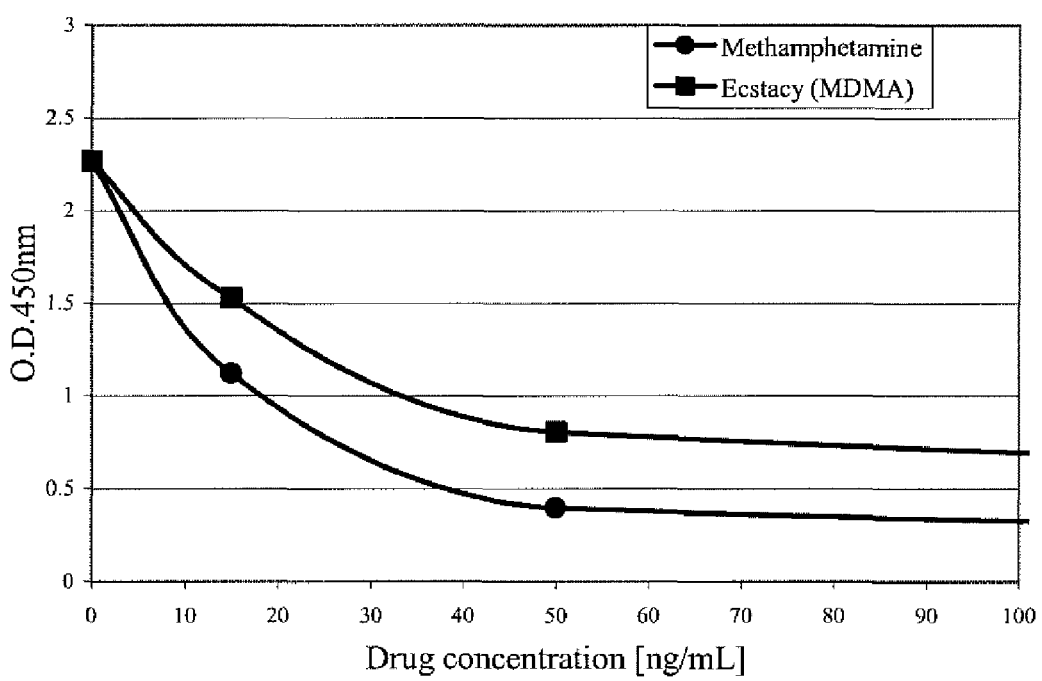
FIG. 3: Typical standard curves obtained by competitive ELISA according to the invention for methamphetamine and ecstasy.

Competitive ELISA was then set up to evaluate the cross-reactivity of various drugs with methamphetamine. The immunoassay was performed as above with the following variations: after coating and blocking microtitre wells with BSA-pseudoephedrine, anti-methamphetamine antibody (1.5 :g/ml in assay buffer, 100 :l/well were co-incubated with varying concentrations of the drugs in assay buffer (25 :l/well) and the assay performed as above. Cross-reactivity was determined using standard curves constructed with (+)- methamphetamine or ecstasy (DMA) at 0, 15, 50 and 500 ng/mL. FIG. 3 shows typical standard curves. Table 1 lists the cross-reactivity obtained with a number of compounds. It is quite apparent the lack of reactivity of this assay with both isomers of ephedrine and pseudoephedrine (<0.1%). The designer ecstasy drugs MDMA and MBDB were well detected by this assay. Amphetamine, tyramine and phenylpropanolamine showed very low cross-reactivity in this assay (amphetamine <0.4%; tyramine and phenylpropanolamine <0.1%).

TABLE 1

| Compound | Concentration [ng/ml] | Concentration determined by ELISA [ng/ml] | % Cross-reactivity |
|---|---|---|---|
| (+)-ephedrine | 10,000 | 8.37 | 0.08 |
| (−)-ephedrine | 10,000 | 5.05 | 0.05 |
| (+)-pseudoephedrine | 10,000 | 6.3 | 0.063 |
| (−)-pseudoephedrine | 10,000 | 4.84 | 0.048 |
| phenylpropanolamine | 10,000 | 5.8 | 0.06 |
| tyramine | 10,000 | 3.72 | 0.03 |
| phentermine | 50,000 | 4.67 | 0.009 |
| (+)-amphetamine | 10,000 | 37.97 | 0.379 |
| MDA | 10,000 | 21.94 | 0.219 |
| beta-phenylethylamine | 10,000 | 25.6 | 0.25 |
| MDMA (Ecstasy) | 15 | 8.26 | 55.0 |
|  | 50 | 24.09 | 48.1 |
|  | 100 | 53.19 | 53.19 |
| MBDB | 25 | 18.76 | 75.04 |
|  | 100 | 66.43 | 66.43 |
|  | 500 | 438.88 | 87.78 |
| MDEA | 25 | 2.67 | 10.66 |
|  | 100 | 4.03 | 4.028 |
|  | 500 | 15.59 | 3.117 |

These results demonstrate that such an enzyme immunoassay has sufficient sensitivity to be used for assaying all types of biological matrices for the presence of methylamphetamine-like drugs, e.g., urine, blood, sweat, hair and oral fluid.

Example 6

Figure 4:
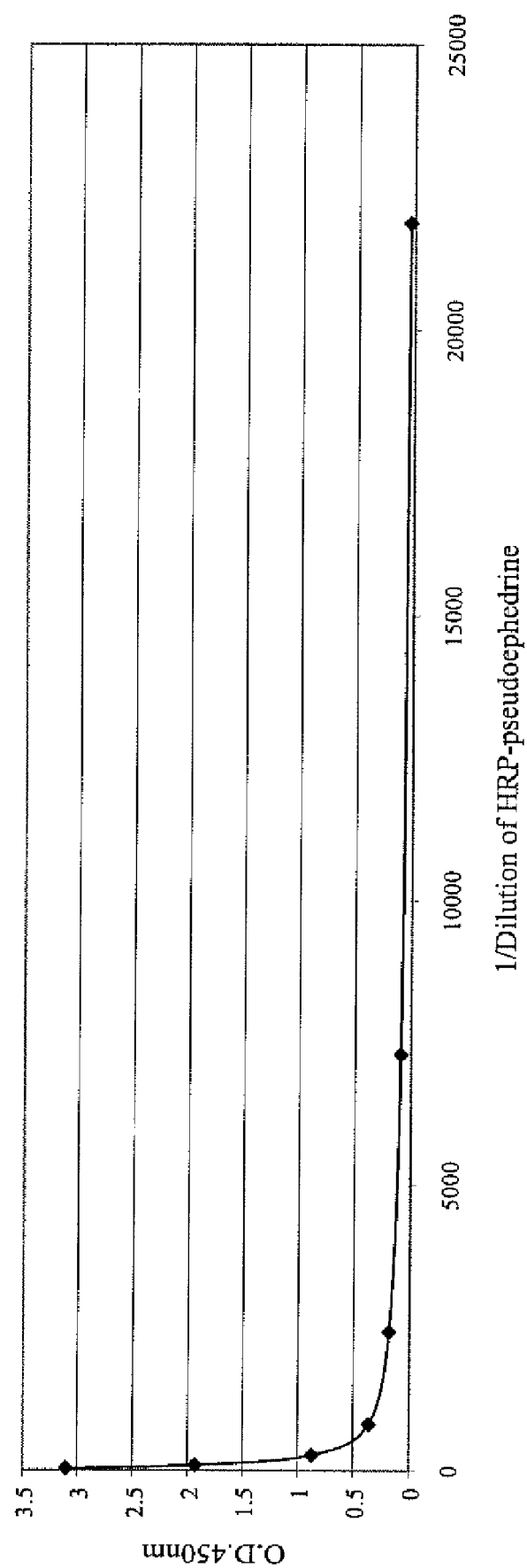
FIG. 4: Titration profile of horseradish peroxidase-pseudoephedrine versus immobilised anti-methamphetamine antibody.

Evaluation of Horseradish Peroxidase-Pseudoephedrine Conjugate by Enzyme Immunoassay 96-well microtitre plates were coated overnight at room temperature with monoclonal anti-methamphetamine antibody (East Coast Biologicals, USA) at 5 :g/ml, 100 :l/well, in 50 mM sodium carbonate/bicarbonate buffer, pH 9.6. The plate was washed 3 times with wash buffer and blocked in the same buffer for 30 minutes. 3-fold dilutions in assay buffer of the enzyme-drug conjugate (100 :l/well) were added. After 30 minutes incubation at room temperature, the plate was washed 3 times and the substrate solution added as described before. FIG. 4 shows the titration profile obtained with this conjugate. The conjugate retained both enzyme activity and the ability to bind to immobilised anti-methamphetamine antibody allowing its use in drug capture competitive enzyme immunoassay.

Example 7

Figure 5:
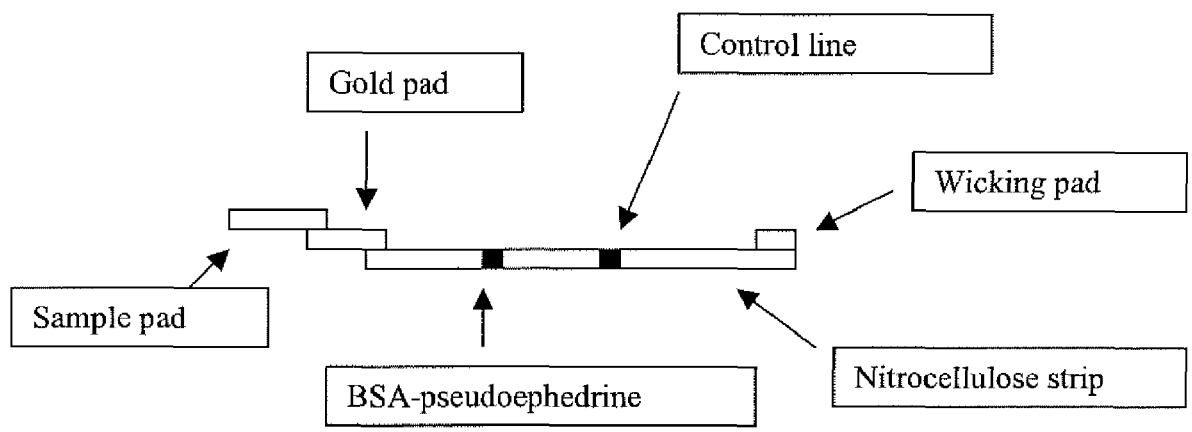
FIG. 5: Diagram illustrating a lateral flow test strip for use in carrying out a lateral flow immunochromatography assay according to the invention in which (1) is a porous strip of nitrocellulose sheet laminated onto a backing support, (2) is the analyte detection zone presenting immobilised BSA-pseudoephedrine, (3) is the control zone presenting immobilised antibody to capture labelled antibody, (4) is a label release pad which releases labelled antibody into liquid drawn into this pad from the sample receiving pad (5) and (6) is a wicking pad.

Point-of-Care Lateral Flow Immunochromatography Test for Methamphetamine/Ecstasy Lateral flow strip tests for methamphetamine/ecstasy were developed using the methodology as described in GB Patent 2339615 and Journal of Forensic Science, 2001, 46:1214-1220. FIG. 5 shows a final strip format including a strip consisting of nitrocellulose sheet laminated onto a backing support (1). Sheep anti-mouse IgG antibody at 0.5 mg/ml and BSA-pseudoephedrine at 1 mg/ml, both in phosphate buffered saline, pH 7.3 containing 0.05% sodium azide, were immobilised on to the strip by spraying, using inkjet or direct contact techniques, as two lines (the analyte detection zone presenting immobilised conjugate (2) and the control zone presenting immobilised antibody (3)). A glass fibre pad (4) containing dried gold-labelled mouse anti-methamphetamine antibody in buffer and detergent was laminated in contact with the nitrocellulose at the end nearest to the drug-conjugate line. A sample receiving pad (5) was laminated in contact with the gold pad. A wicking pad (6) was placed at the distal end. The strip was assembled into a plastic casing.

The test was initiated by the addition of oral fluid diluted in saliva diluent buffer (Cozart Oral Fluid Dilution Buffer, Cozart Bioscience product CR-BUFF) on to the sample pad. The liquid moved across the strip hydrating the gold-labelled antibody. Sample and gold-labelled antibody then moved across the nitrocellulose strip allowing the gold-labelled antibody to bind to the immobilised pseudoephedrine/carrier conjugate forming a red-brownish line. The immobilised sheep anti-mouse IgG antibody (control line) captured excess gold-labelled antibody. If the sample contained methamphetamine or related cross-reacting drug, the gold-labelled antibody bound to this drug resulting in reduction in the intensity or absence of drug line.

The result of the test was read after completion (3-5 minutes) using a Cozart Rapiscan reader that reports the result as negative or positive against a pre-set line intensity value (cut off point). The cut off point was set so that samples containing ≥15 ng/ml of (+)-methamphetamine would be read as positive. Such a test may also be designed to be read visually where, for a given concentration cut-off value a negative sample would correspond to a line and a positive sample would give no line for the drug. The cross-reactivity of the test strip was determined by collecting saliva from drug-free volunteers by expectoration. The saliva was spiked with a variety of drugs, diluted with saliva diluent buffer and tested using identical strips. Table 2 shows the results. None of the ephedrine class of compounds gave positive results at the concentrations tested. In addition to methamphetamine, the test picked up related drugs like ecstasy and MBDB but not amphetamine-like drugs. It is also worth noticing that no sample pre-treatment was required to eliminate undesirable cross-reactivity with ephedrine-like compounds.

TABLE 2

Cross-reactivity of compounds in the methamphetamine/ecstasy lateral flow test. All compounds were tested at 10,000 ng/ml unless otherwise stated

| Compound | | Lateral flow test result |
|---|---|---|
| (+)- methylamphetamine | 15 ng/ml | positive |
| (DL)-MDMA (Ecstasy) | 30 ng/ml | positive |
| MBDB | 15 ng/ml | positive |
| MDEA | 250 ng/ml | positive |
| MDA | | negative |
| (+)- ephedrine | | negative |
| (−)- ephedrine | | negative |
| (+)-pseudoephedrine | | negative |
| (−)- pseudoephedrine | | negative |
| Phenylpropanolamine | | negative |
| Tyramine | | negative |
| Fenfluramine | | negative |
| Ranitidine | | negative |
| Chlorpheniramine | | negative |

TABLE 2-continued

Cross-reactivity of compounds in the methamphetamine/ecstasy lateral flow test. All compounds were tested at 10,000 ng/ml unless otherwise stated

| Compound | Lateral flow test result |
|---|---|
| Pheniramine | negative |
| β-phenylethylamine | negative |
| Ketamine | negative |
| Amphetamine | negative |

The invention claimed is:

1. A method for detecting whether a liquid sample contains one or more drugs of the methamphetamine group comprising:
   (a) contacting said sample with (i) a pseudoephedrine/carrier conjugate in which pseudoephedrine is linked via its hydroxyl group to the carrier and (ii) an antibody which is capable of binding both one or more drugs of the methamphetamine group and said conjugate; and
   (b) determining whether the binding of said antibody to said conjugate is reduced by the presence of said sample, a reduction in binding being indicative that the sample contains a methamphetamine group drug.

2. The method according to claim 1 wherein said antibody is capable of specifically binding to the group of drugs consisting of methamphetamine, ecstasy (3,4-methylenedioxymethamphetamine, MDMA), (+/−)-N-methyl-1-(3,4-methylenedioxyphenyl)-2-butanamine (MBDB) and (+/−)-3,4-methylenedioxyethylamphetamine (MDEA).

3. The method as claimed in claim 2 wherein at least methamphetamine, ecstasy (3,4-methylenedioxymethamphetamine, MDMA) and (+/−)-N-methyl-1-(3,4-methylenedioxyphenyl)-2-butanamine (MBDB) are capable of detection at at least 15 ng/ml.

4. The method according to claim 1 wherein said antibody has less than 0.4% cross-reactivity with all of (+)-ephedrine, (−)-ephedrine, (+)-pseudoephedrine, (−)-pseudoephedrine, phenylpropanolamine, phentermine, tyramine, amphetamine, beta-phenylethylamine and MDA at a concentration of 10,000 ng/ml.

5. The method as claimed in claim 4 wherein said antibody has less than 0.1% cross-reactivity with all of (+)-ephedrine, (−)-ephedrine, (+)-pseudoephedrine, (−)-pseudoephedrine, phenylpropanolamine, phentermine and tyramine at a concentration of 10,000 ng/ml.

6. The method according to claim 1 wherein said carrier is a protein.

7. The method according to claim 6 wherein said protein is selected from bovine serum albumin, horseradish peroxidase, ovalbumin, a gamma globulin and thyroglobulin.

8. The method according to claim 1 wherein said carrier is a homo- or hetero-amino acid polymer.

9. The method according to claim 1 wherein said antibody is labeled directly or indirectly.

10. The method according to claim 1 wherein said pseudoephedrine conjugate is labeled directly or indirectly or the carrier of said conjugate also serves as a detectable label.

11. The method according to claim 1 wherein said conjugate is a conjugate obtained by coupling pseudephedrine via its hydroxyl group to said carrier using dimethyl aminopyridine/disuccinimidyl carbonate, formaldehyde or vinyl sulfone.

12. The method according to claim 1 wherein the pseudoephedrine is coupled to said carrier via a spacer molecule.

13. The method according to claim 1 wherein one of said antibody and said pseudoephedrine/carrier conjugate is immobilised on a solid support.

14. The method according to claim 13 wherein the pseudoephedrine/carrier conjugate is immobilized on a solid support and said antibody is labeled with a detectable label.

15. The method as claimed in claim 13 which is conducted using a lateral flow immunochromatography assay device.

16. The method as claimed in claim 1 wherein said sample consists of, or is derived from, urine, blood, sweat, oral fluid or hair.

17. The method as claimed in claim 1 wherein said sample is a sample obtained by dissolving a powder to be tested in a buffer solution.

18. A test strip or sheet for use in a lateral flow analytical device for carrying out a lateral flow immunochromatography assay according to claim 15, said test strip or sheet comprising:
   (i) a strip or sheet comprising a dry porous material having immobilised thereon in an analyte detection zone said pseudoephedrine/carrier conjugate or said antibody and
   (ii) joined to, or integral to, said strip or sheet providing said analyte detection zone a separate label release zone which is capable of releasing into liquid drawn into the zone either said antibody in labeled form, if said analyte detection zone presents immobilised pseudoephedrine conjugate, or, if said analyte detection zone presents immobilised antibody, detectable pseudoephedrine conjugate, wherein the pseudoephedrine conjugate is labeled directly or indirectly or the carrier of said conjugate also serves as a detectable label.

19. The test strip or sheet according to claim 18 wherein said dry porous material is nitrocellulose.

20. The test strip or sheet according to claim 18 wherein pseudoephedrine/carrier conjugate is immobilised in an analyte detection zone.

21. The test strip or sheet according to claim 18 which further comprises a control zone which is located distal to said analyte detection zone in the direction of intended liquid flow, wherein said control zone comprises an immobilized reagent that binds to either labeled antibody or detectable pseudoephedrine conjugate.

22. The test strip or sheet according to claim 18 which further comprises a sample receiving member or pad proximal to said label release zone having regard to the intended direction of liquid flow.

23. The test strip or sheet as claimed in claim 18, wherein said test strip or sheet is disposed in a housing.

24. The test strip or sheet according to claim 18, wherein said test strip or sheet is disposed in a lateral flow device.

25. A kit for carrying out a method according to claim 1 which comprises said pseudoephedrine/carrier conjugate and said antibody.

26. The kit as claimed in claim 25 wherein said antibody is directly labeled or secondary labeled antibody is provided for labeling of said antibody.

27. The kit as claimed in claim 25 wherein said conjugate is a detectable conjugate.

28. The kit as claimed in claim 25 wherein said antibody or said conjugate is immobilised on a solid support.

29. The kit as claimed in claim 28 which comprises a test strip or sheet, wherein said test strip or sheet comprises:
   (i) a strip or sheet comprising a dry porous material having immobilised thereon in an analyte detection zone said pseudoephedrine/carrier conjugate or said antibody and
   (ii) joined to, or integral to, said strip or sheet providing said analyte detection zone a separate label release zone which is capable of releasing into liquid drawn into the zone either said antibody in labeled form, if said analyte detection zone presents immobilised pseudoephedrine conjugate, or, if said analyte detection zone presents immobilised antibody, detectable pseudoephedrine conjugate, wherein the pseudoephedrine conjugate is labeled directly or indirectly or the carrier of said conjugate also serves as a detectable label.

30. The test strip or sheet according to claim 18 which further comprises an absorbent waste pad distal to said analyte detection zone in the direction of intended liquid flow.

* * * * *